(12) United States Patent
Hoenig et al.

(10) Patent No.: US 7,744,592 B2
(45) Date of Patent: Jun. 29, 2010

(54) APPARATUS AND METHOD FOR THE TREATMENT OF INFECTIOUS DISEASE IN KERATINIZED TISSUE

(75) Inventors: Peter A. Hoenig, Sudbury, MA (US); B. Stuart Trembly, Hanover, NH (US)

(73) Assignee: Waverx, Inc., Waltham, MA (US)

( * ) Notice: Subject to any disclaimer, the term of this patent is extended or adjusted under 35 U.S.C. 154(b) by 1273 days.

(21) Appl. No.: 10/990,283

(22) Filed: Nov. 16, 2004

(65) Prior Publication Data

US 2005/0137654 A1    Jun. 23, 2005

Related U.S. Application Data

(63) Continuation-in-part of application No. 10/845,761, filed on May 14, 2004, now Pat. No. 7,292,893, and a continuation-in-part of application No. 10/845,010, filed on May 13, 2004, now abandoned.

(60) Provisional application No. 60/471,230, filed on May 16, 2003.

(51) Int. Cl.
*A61B 18/04* (2006.01)
(52) U.S. Cl. .............................. 606/33; 607/101; 607/96
(58) Field of Classification Search .................. 607/96, 607/101–102; 606/41–50, 33
See application file for complete search history.

(56) References Cited

U.S. PATENT DOCUMENTS

| | | | |
|---|---|---|---|
| 4,016,886 A | 4/1977 | Doss et al. | |
| 4,092,800 A | 6/1978 | Wayland, Jr. et al. | |
| 4,203,549 A | 5/1980 | Paglione | |
| 4,312,364 A | 1/1982 | Convert et al. | |
| 4,448,198 A | 5/1984 | Turner | |
| 4,471,787 A * | 9/1984 | Bentall ...................... | 607/154 |
| 4,679,561 A | 7/1987 | Doss | |
| 4,702,262 A | 10/1987 | Andersen et al. | |
| 4,825,880 A | 5/1989 | Stauffer et al. | |
| 4,881,453 A | 11/1989 | Armstrong | |
| 4,932,420 A | 6/1990 | Goldstein | |
| 4,967,765 A | 11/1990 | Turner et al. | |
| 5,248,478 A | 9/1993 | Kutner et al. | |
| 5,370,676 A | 12/1994 | Sozanski et al. | |
| 5,470,332 A * | 11/1995 | Mehl et al. ..................... | 606/36 |
| 5,708,445 A | 1/1998 | Moller et al. | |
| 6,006,136 A | 12/1999 | Glucksman | |
| 6,051,018 A | 4/2000 | Larsen | |

(Continued)

FOREIGN PATENT DOCUMENTS

DE    1130534    5/1962

(Continued)

OTHER PUBLICATIONS

Tanaka, Y. et al. *Yonaga Acta Medica*, 41: 83-88, 1998.

(Continued)

*Primary Examiner*—Roy D Gibson
(74) *Attorney, Agent, or Firm*—Lando & Anastasi, LLP

(57) ABSTRACT

Apparatus and methods for the treatment of keratinized tissue infected with a pathogen are provided. In certain examples, electromagnetic energy, such as microwave energy, may be used in the treatment process to reduce the amount of or eliminate the pathogen from the keratinized tissue.

27 Claims, 9 Drawing Sheets

U.S. PATENT DOCUMENTS

| | | | |
|---|---|---|---|
| 6,056,744 | A | 5/2000 | Edwards |
| 6,090,788 | A | 7/2000 | Lurie |
| 6,104,959 | A | 8/2000 | Spertell |
| 6,254,389 | B1 | 7/2001 | Seghatol |
| 6,413,255 | B1 * | 7/2002 | Stern ............................ 606/41 |
| 6,453,202 | B1 * | 9/2002 | Knowlton ................... 607/102 |
| 6,463,336 | B1 | 10/2002 | Mawhinney |
| 6,527,767 | B2 * | 3/2003 | Wang et al. .................... 606/32 |
| 6,635,055 | B1 | 10/2003 | Cronin |
| 6,696,677 | B2 | 2/2004 | Kennedy |
| 6,723,090 | B2 | 4/2004 | Altshuler et al. |
| 6,878,147 | B2 | 4/2005 | Prakash et al. |
| 2002/0128642 | A1 | 9/2002 | Berube et al. |
| 2002/0169442 | A1 | 11/2002 | Neev |
| 2003/0153962 | A1 | 8/2003 | Cumbie |
| 2003/0180181 | A1 | 9/2003 | Greib et al. |
| 2004/0093042 | A1 | 5/2004 | Altshuler et al. |
| 2005/0080465 | A1 | 4/2005 | Zelickson et al. |
| 2009/0281537 | A1 * | 11/2009 | Britva et al. .................. 606/33 |

FOREIGN PATENT DOCUMENTS

| | | |
|---|---|---|
| EP | 04811065.4 | 8/2008 |
| GB | 748216 | 4/1956 |
| WO | 0023147 | 4/2000 |
| WO | 03003903 | 1/2003 |
| WO | 03069310 | 8/2003 |
| WO | 2004103298 | 12/2004 |

OTHER PUBLICATIONS

Korpan, N. et al. *J. Surg. Res.*, 57(6): 667-71, Dec. 1994.
Deacon, J.W. *Introduction to Modern Mycology*. 2$^{nd}$ Ed. Blackwell Scientific Pubs, 1984.
Bold, H.C. et al. *Morphology of Plants and Fungi*, 5$^{th}$ Ed. (1987).
Moritz and Henriques. *Am. J. Pathology*. 23: 695-720 (1947).
Song, C.W. "Role of Blood Flow in Hyperthermia." in M. Urano and E.B. Douple (Eds.), *Hyperthermia and Oncology vol. 3: Interstitial Hyperthermia—Physics Biology and Clinical Aspects*. Utrecht, the Netherlands, VSP BV, 1992.
Dahl (Dahl, O.) "Interaction of Heat and Drugs In Vitro and In Vivo," *Thermoradiotherapy and Thermochemotherapy, vol. 1: Biology, Physiology and Physics*. Berlin: Springer-Verlag, 1995.
Ryan, T.P., "Comparison of Six Microwave Antenna for Hyperthermia Treatment of Cancer: SAR Results for Single Antennas and Arrays," *Int. J. Radiation Oncology, Biology and Physics*, 21: 403-413, 1991.
Baker et al. (1969) PhytopathologyPhytopathology 59(2) 193-197.
Swicord et al. (1981) IEEE Trans. On Microwave Theory and Techniques 29(11): 1202-1208.
Ludeke et al. (1983) Journal of Microwave Power 18(3): 277-283.
Trembly et al. (1991) IEEE Transactions On Biomedical Engineering 28(1) 85-91.
Lagunas-Solar et al. (1994) Annual International Research Conference on Methyl Bromide Alternatives and Emissions Reductions, Nov. 13-16, Kissimmee, Florida.
Ramo et al. Fields and Waves in Communication Electronics. 3$^{rd}$ Ed. (New York, 1994).
Jones et al. (1995) Pacific Rim Biotechnology Conference Melbourne, Australia, Feb. 1995.
Ferreira et al. (1996) Fungal Genetics Newsletter 43: 25-26.
Guyton et al. (1996) Textbook of Medical Physiology p. 919.
Lantis et al. (1998) Surg. Endosc. 12:170-176.
Tanaka et al. (1998) Yonaga Acta Medica 41:83-88.
Hay (2001) British Journal of Dermatology 145 (S60):3-11.
Mandell et al. Principles and Practice of Infectious Diseases, Fifth Edition, Chapter 257 by Hay, R.J., p. 2765.

* cited by examiner

APPARATUS AND METHOD FOR THE TREATMENT OF INFECTIOUS DISEASE IN KERATINIZED TISSUE

PRIORITY APPLICATIONS

This application is a continuation-in-part of U.S. application Ser. No. 10/845,761 filed on May 14, 2004, now U.S. Pat. No. 7,292,893, and is a continuation-in-part of U.S. application Ser. No. 10/845,010, filed on May 13, 2004, now abandoned, each of which claims priority to U.S. provisional application No. 60/471,230, filed May 16, 2003, and the entire disclosure of each of which is hereby incorporated herein by reference for all purposes.

FIELD OF THE TECHNOLOGY

Certain examples relate to the field of medicine, particularly the treatment of infectious diseases. More specifically, certain examples relate to treatment of keratinized tissue infected with a pathogen.

BACKGROUND

Infectious diseases of keratinized tissues are a difficult problem for medical treatment. Keratins are a class of scleroprotein that serve as the major protein components of hair, wool, nails, the organic matrix of the enamel of teeth, horns, hoofs, and the quills of feathers. These proteins generally contain large quantities of the sulfur-containing amino acids, particularly cysteine. Keratins provide a tough, fibrous matrix for the tissues in which they are found. These proteins are characterized as being extremely water insoluble. Because keratins contain few polar amino acids, there is little or no moisture content in the tissues they form. This presents difficulties for the medical treatment of infected keratinized tissues because medicaments are not easily delivered into this type of tissue.

By way of example, onychomycosis is clinically defined as an infection of the nail plate caused by any fungus, including dermatophytes, non-dermatophytes and yeasts. This disease accounts for up to 50% of all nail disease and affects 2% to 18% or more of the world's population. There are four clinical types of onychomycosis: (1) distal subungual onychomycosis, (2) proximal subungual onychomycosis, (3) white superficial onychomycosis, and (4) candidal onychomycosis. The target sites for the treatment of onychomycosis reside in the nail plate, nail bed and nail matrix. Characteristically, infected nails coexist with normal-appearing nails.

The most common form of treatment for onychomycosis is the oral administration of terbinafine (Novartis International AG, Basel, Switzerland) or itraconazole (Janssen Pharmaceutical Products, L.P., Titusville, N.J.). These drugs dominate the current market for the treatment of onychomycosis.

However, there is a need for the development of other forms of treatment. Hay, R J (*British Journal of Dermatology* 145(S60):3-11, 2001) teaches that these drugs have a clinical failure rate of approximately 25-40%. In addition, both drugs carry label precautions about potential organ toxicity and interactions with common prescription and non-prescription drugs. The Physicians Desk Reference (2003) teaches that rare cases of hepatic failure (including death) have been reported following oral treatment with Terbinafine and Itraconazole. Rare cases of serious cardiovascular events, including death, also have been associated with Itraconazole (Id.). Treatment times are long (several months) and costly. Hay, 2001 teaches that 5-10% of the nail surface still remains abnormal even with a full cure (defined by negative re-culturing). Mandell et al (*Principles and Practice of Infectious Diseases*, Fifth edition, Chapter 257 by Hay R. J., p. 2765, 2000) teach that the relapse rate is 40%. Treatment options using topical agents are usually of little benefit, and chemical or surgical removal of the infected nail(s) are not adequate therapies, since these treatments can lead to nail bed shrinkage and dorsal dislocation of the nail bed.

Thus, there remains a need in the art to develop improved methods for the treatment of keratinized tissue infected with a pathogen.

SUMMARY

Certain aspects and examples described herein provide an apparatus and methods for the medical treatment of keratinized tissue infected with a pathogen. The methods according to the invention enable an efficacious, localized, speedy, and non-invasive medical treatment with little or no side effects.

In a first aspect, a method of treating keratinized tissue infected with a pathogen is provided. In certain examples, the method comprises exposing the keratinized tissue to an effective amount of electromagnetic energy having a wavelength greater than about 0.0004 mm, e.g., microwave energy or millimeter wave energy, sufficient to kill the pathogen infecting the keratinized tissue. In a particularly preferred embodiment, the keratinized tissue is human keratinized tissue, e.g., nail tissue, infected with a pathogen. In one specific embodiment, the nail tissue is human nail tissue. In certain embodiments, the electromagnetic energy is microwave energy, e.g., microwaves having frequencies of about 15 MHz to about 30 GHz, or millimeter wave energy.

In a second aspect, an applicator for the delivery of electromagnetic energy to keratinized tissue infected with a pathogen is disclosed. In certain examples, the applicator comprises one or more conductors configured to deliver energy to the anatomical site. In certain embodiments, a pair of conductors has a coaxial cable geometry. In one embodiment, the outer conductor of a coaxial cable has been removed for part of its circumference to expose tissue in proximity to the applicator to electromagnetic energy. In another embodiment, the inner conductor of the coaxial cable geometry is connected to a disk at its terminal end to form an end-loaded monopole that transfers energy efficiently to tissue in proximity to the applicator. In some embodiments, the applicator further comprises a cable, e.g., coaxial cable, and an electromagnetic energy source.

BRIEF DESCRIPTION OF THE DRAWINGS

Certain illustrative examples and embodiments are described below with reference to the accompanying figure in which.

DETAILED DESCRIPTION

Figure 1:
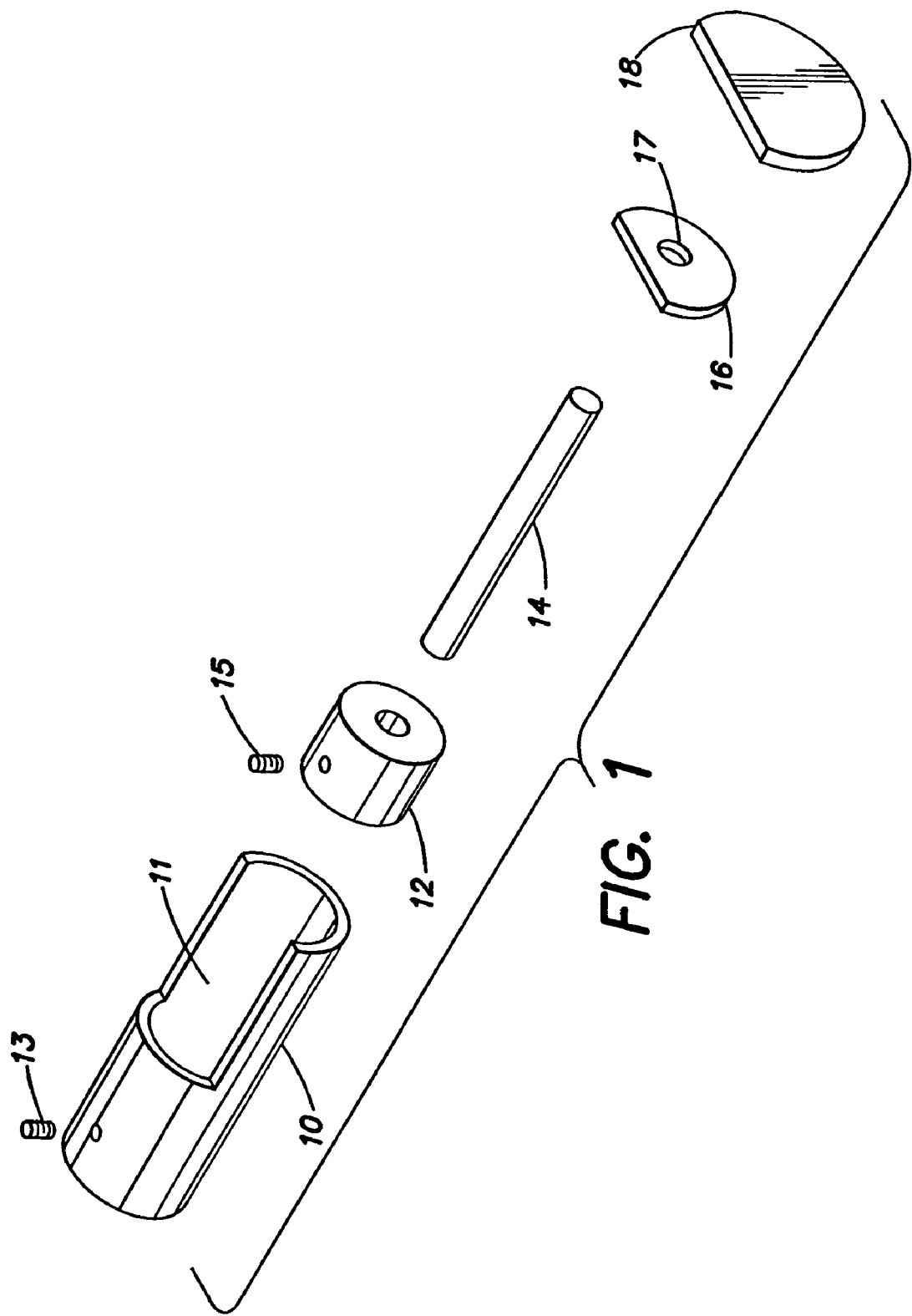
FIG. 1 is an exploded view of one example of an applicator, in accordance with certain examples of aspects of the invention.

Certain examples disclosed herein provide significant advances in the treatment of keratinized tissues not heretofore recognized by practitioners. For example, it was a surprising discovery that the high water content of fungi, bacteria, and parasites relative to keratinized tissue renders the fungi, bacteria, and parasites sensitive to electromagnetic energy, particularly microwave energy. Such application of energy can result in "superheating" and explosion of the bacterial, fungal, or parasitic cells. Certain examples of the methods described herein do not rely on an electrical conduction current flowing through tissue between two or more metallic conductors in direct contact with tissue (resistive heating). Instead, examples of the methods described herein use an electric field of electromagnetic energy, e.g., microwave energy, to penetrate into tissue. The rapidly-oscillating field in tissue causes polar molecules, such as water in fungal, bacterial, or parasite cells, to rotate in place, thereby producing local frictional heating. Without wishing to be bound by any particular scientific theory or this example, the pathogens are destroyed when the heating process has sufficient magnitude and duration. The penetrating electric field permits transmission of energy through tissue of low water content, which can effectively be an electrical insulator. In this way, a penetrating electric field of electromagnetic energy applied, for example, at the surface of the nail plate, which has low water content, can sterilize a pathogen below the surface of the nail plate. In contrast, a conduction current, e.g., a radio frequency current, applied to the nail plate would have little or no heating effect on a pathogen below the nail plate.

Advantages of the use of electromagnetic energy, e.g., microwave energy, are the speed, efficiency, localized effect, ability to intervene without surgery, rapid patient recovery, and absence of toxic, hazardous or polluting residues. Further advantages are the stimulation of the immune system to assist in the destruction of pathogens and the stimulation of blood perfusion in nearby tissues to enhance the delivery of agents of the immune system to, or near, the site of pathogen infection.

Microwave irradiation is an efficient means of sterilization. For example, U.S. Pat. No. 4,092,800 teaches the sterilization of soil with microwave irradiation. Baker, K F et al (*Phytopathology* 59(2):193-197, 1969) teach the sterilization of garbage with microwave irradiation. Lagunas-Solar M. C. et al (Food and Agriculture Applications of Pulsed Power Technologies as Alternatives to Methyl Bromide, 1994 Annual International Research Conference on Methyl Bromide Alternatives and Emissions Reductions. Nov. 13-16, 1994) teach the sterilization of food with microwave irradiation. Kissimme et al. (*Yonaga Acta Medica* 41:83-88, 1998) teach the sterilization of towels with microwave irradiation.

Lantis, J C (*Surg. Endosc.* 12:170-176, 1998) teach that microwave energy has been used in medicine for many clinical applications since the development of reliable magnetrons in the 1960's. For example, microwave energy therapy has been used for the treatment of malignant and benign neoplasia. It is being explored as a modality to improve the healing of infected wounds. It is being studied as a therapy for the treatment of duodenal ulcer disease, benign prostatic hypertrophy and for heart disease. Microwave energy is also being used to warm dialysate fluid for continuous ambulatory peritoneal dialysis and as a way to sterilize docking connectors.

Unlike resistance that organisms may develop to therapeutics, fungi, bacteria, or parasites are unlikely to develop resistance to the methods of treatment provided herein. There have been no reports of fungi, bacteria, or parasites developing resistance to, for example, microwave energy. In fact, microwave heating has been used to treat infected wounds. Korpan, et al.(Korpan N N, Resch K L, & Kokoschinegg P, "Continuous microwave enhances the heating process of septic and aseptic wounds in rabbits" *Journal of Surgical Research* 57(6): 667-671, December 1994.) teach that microwave irradiation at an intensity of 1 mW/cm$^2$ at a frequency of 37 GHz stimulates the immune system and enhances the healing process of wounds.

Deacon, J W ("Introduction to Modern Mycology", 2nd Edition. Blackwell Scientific Publications. 1984) teaches that most fungi have a tough, protective wall that surrounds the protoplasm within the fungal cell. Several fungi have pigments in this wall that protects the cell interior against damage from ultra-violet (UV) light. Microwave energy can penetrate the protective wall to overheat the high-water-content protoplasm within and thus kill the fungal cell. The pigments that block UV light have no effect on microwave energy.

Microwave energy is a safer treatment modality for infection by pathogen than UV light, because it does not pose the known cancer risk that UV light does for skin tissue.

Referring now to FIG. 1, an exploded view of an embodiment of an applicator is shown. Outer conductor 10 may be made of an electrical conductor, such as aluminum, copper, or brass; in this embodiment, it has the shape of a cylindrical shell with a portion of the circumference cut away. Other suitable shapes, however, will be readily selected by the person of ordinary skill in the art, given the benefit of this disclosure. In the example shown in FIG. 1, conductor 10 may have an opening 11 that has a length and breadth about equal to the length and breadth of the anatomical site to be treated. Conductor 10 may slide onto internal spacer 12, which has the shape of a cylinder; it may be made of an insulating material, such as nylon, PTFE or other suitable insulating materials. Conductor 10 may be secured to spacer 12 by means of a set screw 13. Inner conductor 14 may have the shape of a rod, and it may slide into spacer 12; conductor 14 is typically made of an electrical conductor, such as aluminum, copper, gold, brass or other suitable conductive materials that will be readily selected by the person of ordinary skill in the art, given the benefit of this disclosure. Conductor 14 may be fixed to spacer 12 by means of a set screw 15, which can be made of plastic, or other suitable material, to prevent a short circuit between conductors 10 and 14. Conductor 14 can pass through hole 17 in cap spacer 16, and then may continue to make electrical contact with end cap 18. Cap spacer 16 and end cap 18 generally have the shape of a section of a disk. Cap spacer 16 may be made of an electrical insulator, such as delrin or PTFE. End cap 18 may be made of an electrical conductor, such as aluminum, copper, gold, brass, etc. Conductor 14 may be fixed to end cap 18 by a means that maintains electrical contact, such as brazing, soldering, or a threaded connector, such as a metal screw (not shown).

Figure 2:
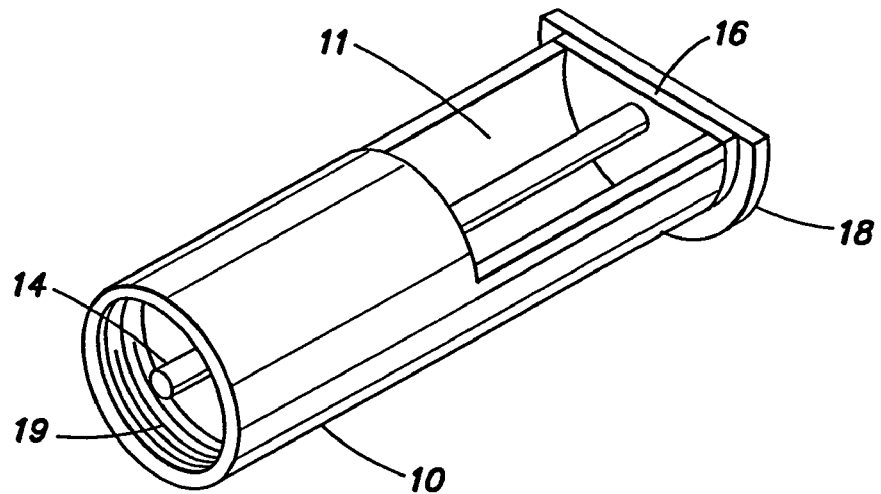
FIG. 2 is a perspective view of the assembled applicator of FIG. 1, in accordance with certain examples of aspects of the invention.

Referring now to FIG. 2, perspective view of the assembled applicator of FIG. 1 is shown. Threading 19 permits the applicator to be connected to a coaxial cable through a connector, such as an N-type connector, or other suitable connector which will be readily selected by the person of ordinary skill in the art, given the benefit of this disclosure. The applicator can be coupled to a source of electromagnetic energy that provides electromagnetic signals, such as in the microwave frequency bands, through the connector and other signal carrying device, such as cables, waveguides, and the like. Inner conductor 14 has a suitable diameter to permit it to connect to the inner conductor of a connector, such as a standard N-type connector; alternatively, the conductor 14 has this diameter only near the end that mates with a standard connector, and conductor 14 may taper or may expand so as to have a different diameter for the rest of its length. In some configurations, the end spacer 16 and end cap 18 may extend to some degree into as plane defined by opening 11, but in the example shown in FIG. 2, end spacer 16 and end cap 18 do not extend into the plane defined by opening 11. This feature permits the tissue to be treated to be placed in juxtaposition with opening 11 without interference. For example, to treat a toe notionally present in FIG. 2 with its nail oriented upwards, the applicator shown in FIG. 2 would be inverted and applied to bring the nail of the toe into juxtaposition with opening 11.

For most of its length, conductor 14 may have a diameter that gives an advantageous value of characteristic impedance in conjunction with the value of the inner diameter of outer conductor 10. As will be recognized by those skilled in the art, given the benefit of this disclosure, the reflection coefficient of the applicator can be reduced when its characteristic impedance is substantially equal to that of a standard coaxial cable connected to it. Again, those skilled in the art will understand, given the benefit of this disclosure, that the end cap 18 may serve to reduce the reflection coefficient of the applicator through capacitive end-loading and thus increase power transfer into tissue placed in proximity to opening 11. U.S. Pat. No. 5,708,445 issued Jan. 13, 1998 to Moller, et al. teaches that a capacitive plate ("top hat") placed near the end of a length of wire reduces the frequency at which the antenna transmits power most efficiently, or equivalently that the top hat antenna functions like a simple wire antenna of greater length. Moller, et al. do not teach the use of a capacitive plate for reducing the reflection coefficient of a coaxial cable with a portion of the circumference removed, as in FIG. 2. The end cap 18 in FIG. 2 reduces the reflection coefficient of the applicator while permitting the applicator to have a truncated length, suitably matched, for example, to the nail of a toe. It is to be appreciated that other devices and techniques for matching an arbitrary load to a source impedance, can be used, and will be readily apparent to the person of ordinary skill in the art, given the benefit of this disclosure.

Figure 3:
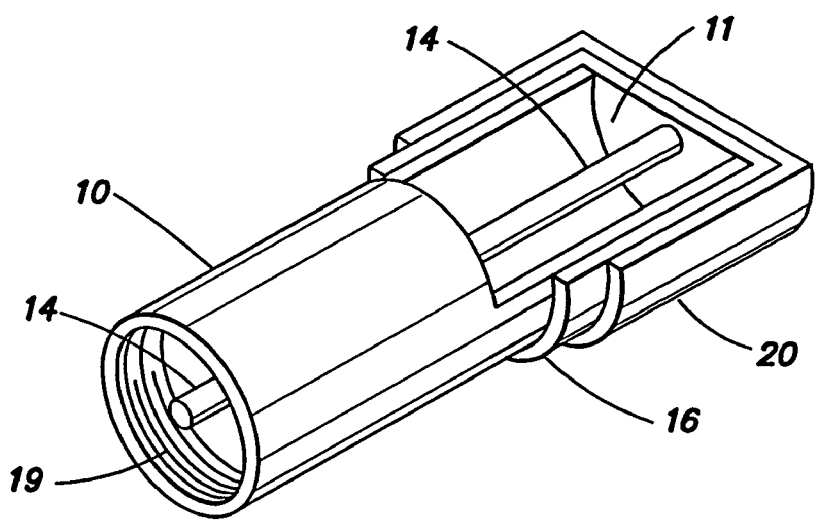
FIG. 3 is a perspective view of an alternative embodiment of the applicator of FIG. 1, in accordance with certain examples of aspects of the invention.

FIG. 3 shows an alternative embodiment, in which the capacitance of the folded end cap 20 is increased by folding it to lie parallel, or substantially parallel, with the long axis of the outer conductor 10. Those skilled in the art will appreciate, given the benefit of this disclosure, that greater capacitance of the end cap may decrease the reflection coefficient of the applicator and that increased capacitance is accomplished in the applicator in FIG. 3 without increasing the diameter of the end cap 18 shown in FIG. 2

In accordance with other embodiments, the pathogen may be a fungus, e.g., the illustrative fungi listed in Bold, H C et al., *Morphology of Plants and Fungi*, $5^{th}$ Ed. (1987). In some embodiments the pathogen may be a bacterium. In some embodiments the pathogen may be a unicellular parasite (protozoa); in some embodiments the pathogen may be a multicellular parasite (helminthes, arthropods). Additional pathogens that cause or contribute to infections of the skin, keratinized tissues, etc. will be readily recognized by the person of ordinary skill in the art, given the benefit of this disclosure.

In some embodiments, the infected keratinized tissue is nail tissue, the corneum stratum of epidermis, hair tissue, hoof tissue, horny tissue, or teeth. In certain embodiments, the infected keratinized tissue is from a mammal, such as for example, human, bovine, or equine tissue. In a particularly preferred embodiment, the keratinized tissue is human keratinized tissue infected with a pathogen. In one specific embodiment, the nail tissue is human nail tissue.

In some embodiments the electromagnetic energy is microwave energy, infrared energy, or millimeter waves. The microwave frequency band is only loosely defined in engineering practice. However unless otherwise clear from the context, it is defined herein to refer to the frequency range from about 15 MHz to about 30 GHz, more particularly about 20 MHz to about 30 GHz, and even more particularly, from about 25 MHz to about 30 GHz. However, other frequencies outside this range are not excluded. As used herein, millimeter waves are defined as having a frequency of about 30 GHz to about 3,000 GHz; the corresponding wavelengths (in vacuum) are about 10 millimeters to about 0.1 millimeters, respectively. As used herein, infrared energy is defined as energy having a wavelength (in vacuum) of about 0.1 millimeters up to about 0.7 microns, where it is customary to define energy in this part of the electromagnetic spectrum in terms of wavelength, as opposed to frequency.

Figure 4:
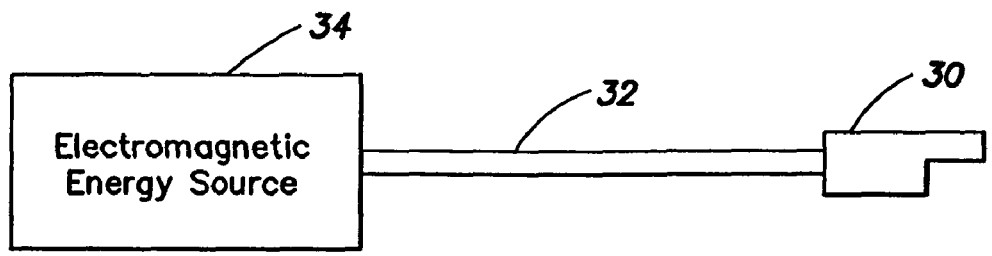
FIG. 4 is a schematic view of an embodiment comprising an applicator, cable, and electromagnetic energy source, in accordance with certain examples of aspects of the invention.

In some embodiments, the applicator further comprises a cable, e.g., a coaxial cable. In some embodiments, the applicator further comprises a cable, e.g., coaxial cable, and an electromagnetic energy source. In certain embodiments, the electromagnetic energy source is selected from the group consisting of a magnetron and a solid state oscillator. In some embodiments, the electromagnetic energy source is sufficiently light and compact to make it portable by hand. FIG. 4 shows applicator 30 connected to cable 32, and cable 32 is connected to electromagnetic energy source 34.

Some embodiments of the methods disclosed herein include applying electromagnetic energy to keratinized tissue when clinical symptoms are not present, e.g., as prophylactic treatment to prevent infection of the keratinized tissue. If pathogens are present, they will be sterilized by the treatment, even though clinical symptoms have not developed. This embodiment of the method of the invention serves to prevent the development of clinical symptoms. The exact treatment frequency may vary depending on numerous factors including, for example, predisposition to infection based on family history, past history of infection, past history of related infection, such as athlete's foot, increased risk for infection, etc. In certain examples, to prevent infection a treatment frequency is about once monthly, biweekly, once weekly or two or three times per week, daily, etc. Additional suitable treatment frequencies will be readily selected by the person of ordinary skill in the art, given the benefit of this disclosure.

Some embodiments of the method and apparatus include stimulation of blood perfusion in tissue in the vicinity of the infected tissue before a treatment with electromagnetic energy by heating the skin surface with a warm fluid or other means. When heating with electromagnetic energy, it is important to limit the thermal dose received by uninfected -tissue. In the case of heating a nail, for example, care should be taken to avoid the derma of the nail bed. Moritz & Henriques (Moritz A R and Henriques F C, "Studies of thermal injury II: The relative importance of time and surface temperature in the causation of cutaneous burns," *The American Journal of Pathology* 23: 695-720, 1947) teach that discomfort in human subjects occurs when skin temperature is elevated to the range 47.5-48.5° C. They also teach that hyperemia without loss of epidermis occurs in human subjects whose skin is exposed to 51° C. for 2 minutes and 49° C. for 6 minutes; these reactions were defined as below the threshold of thermal injury. The characteristic high blood perfusion of skin tissue affords protection from thermal damage because the continuous transport of blood at body temperature into the capillary bed is an effective cooling mechanism. Furthermore, Guyton and Hall, (Guyton A C and Hall J E, *Textbook of Medical Physiology* pg. 919 (Philadelphia: 1996)) teach that perfusion of skin is a function of temperature, increasing as temperature increases. Song (Song C W, "Role of blood flow in hyperthermia," In: M Urano & E B Douple, eds., Hyperthermia and Oncology, Vol. 3: Interstitial Hyperthermia—Physics, Biology, and Clinical Aspects. (Utrecht, the Netherlands: VSP BV, 1992)) teaches that blood perfusion in tissue increases significantly, by as much as a factor of four, with increasing tissue temperature; the same source teaches that the greatest increase in perfusion may occur as much as 30 minutes after the increase in tissue temperature.

In some embodiments, the methods disclosed herein can include the step of inducing reactive hyperemia, wherein blood perfusion after a period of enforced low perfusion increases to a level higher than before the intervention, as taught by Guyton and Hall. In practice, pressure could be applied to the toe to restrict blood perfusion before the heat treatment; alternatively, the limb could be elevated to reduce perfusion. After the release of pressure or removal of elevation, the resulting increased perfusion would provide enhanced cooling during the period of microwave heating.

Figure 5:
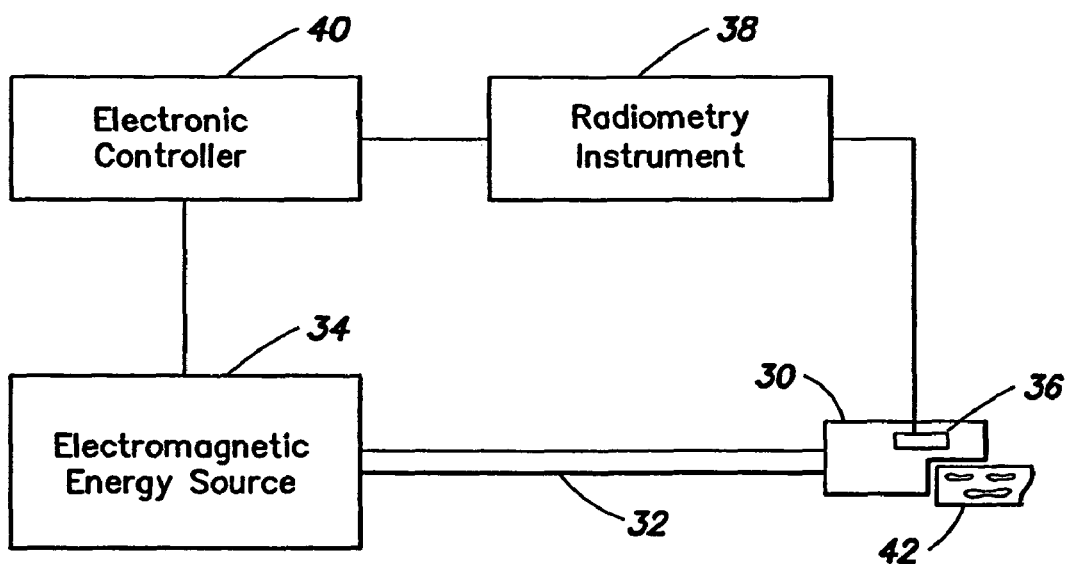
FIG. 5 is a schematic view of an embodiment that includes a radiometry sensor to measure temperature in treated tissue, in accordance with certain examples of aspects of the invention.

In some embodiments of the methods and apparatus disclosed herein, microwave radiometry is used to measure the temperature of tissue heated by electromagnetic energy below the surface of the body. Lüdeke and Küohler (Lüdeke K. M. and Köhler J., *Journal of Microwave Power* 18(3):277-283, 1983) teach that the natural electromagnetic emissions of an object can be correlated with its temperature and that these emissions may come from below the surface of the object. This method could be used to measure the temperature, for example, below the surface of a nail plate being treated for infection by a fungal pathogen. This temperature signal could form part of a feedback loop that could be used to prevent undesired temperature elevation in the nail bed below the nail plate. FIG. 5 shows radiometry receiver 36 inside applicator 30 connected to radiometry instrument 38. Radiometry receiver 36 in combination with radiometry instrument 38 measures the temperature in tissue 42. Radiometry instrument 38 may be connected to electronic controller 40 and to electromagnetic energy source 34, which in turn may be connected to cable 32 and applicator 30. These connected elements form a feedback loop that controls electromagnetic power in response to the temperature measured in tissue 42.

In certain embodiments, the method and apparatus includes placing an electrically-conducting mask over non-infected tissues to substantially block the absorption of microwave energy. Ramo, et al (*Fields and Waves in Communication Electronics*, 3$^{rd}$ Ed. (New York, 1994) teach that a metallic surface approximates a perfect conductor and consequently reflects electric fields from its surface. U.S. Pat. No. 5,248,478 issued Sep. 28, 1993 to Kutner, et al. teaches the use of a metallic shield or reflector to prevent microwave heating of contact lenses in a container used for disinfection. U.S. Pat. No. 6,696,677 issued Feb. 24, 2004 to Kennedy teaches the use of a microwave shield made of metallic foil to divert microwave radiation from certain foods, i.e., reflect the energy, during the process of microwave cooking. In some embodiments, the method and apparatus includes placing metallic paint over non-infected tissues to substantially block the absorption of microwave energy. Neither Kutner nor Kennedy teaches the use of an electrically-conducting mask or reflector to substantially block absorption of electromagnetic energy in selected living tissues.

In certain examples, one or more materials that can absorb or dissipate microwave radiation may be disposed on non-infected tissues to prevent those tissues from being exposed to microwave energy or to reduce the amount of microwave energy that reaches those tissues. While absorption of the microwave energy by the materials may result in some localized heating, such heating generally does not result in any adverse side effects. Suitable microwave energy absorbing materials include, but are not limited to, dyes, foams, tapes with or without metallization, and the like. Additional suitable microwave absorbing materials will be readily selected by the person of ordinary skill in the art, given the benefit of this disclosure.

In certain embodiments, examples of the method and apparatus include the application of electromagnetic energy in conjunction with parenteral, oral, topical, or other suitable administration of one or more other drugs or therapeutics such as the antifungal agents: fluconazole, itraconazole, and terbinafine. Dahl (Dahl, O., "Interaction of heat and drugs in vitro and in vivo," *Thermoradiotherapy and Thermochemotherapy. Vol 1: Biology, Physiology, and Physics*, Seegenschmiedt M H, Fessenden P, and Vernon C C, Eds. (Berlin:

Springer-Verlag, 1995)) teaches that cytotoxic drugs used for cancer therapy can be potentiated by heat treatments. In certain embodiments, the method and apparatus include the administration of one or more suitable drugs or therapeutics in conjunction with electromagnetic energy whose source is sufficiently light and compact to make it portable by hand. It will be recognized by the person of ordinary skill in the art, given the benefit of this disclosure, that use of the methods disclosed herein may allow for lower dosages of existing therapeutics, such that any side effects may be minimized. For example, an effective dose of terbinafine, when administered in conjunction with the methods disclosed herein, may be, for example, 25% lower, 50% lower, or 75% lower (or any range in between) than the effective amount of terbinafine required with terbinafine treatment alone. In some examples, the treatment methods disclosed herein assist the immune system in eradicating any remaining infection, which allows lower amounts of therapeutics, or no therapeutics at all, to be used to eradicate the infection.

In some embodiments, a frequency of electromagnetic energy is chosen to reduce the penetration depth to a desired or selected value. For example, tissue underlying the nail plate could be heated to a toxic temperature in spite of the cooling effect of blood perfusion by energy that penetrated significantly beyond the nail plate. U.S. Pat. No. 6,635,055 issued Oct. 21, 2003 to Cronin teaches that microwave radiation at 8-12 GHz is almost completely absorbed in a layer of tissue about 5 mm thick. At lower frequencies, the depth of penetration is characteristically greater. Ramo et al. teach, for example, that the depth of penetration of a plane wave of 915 MHz radiation in soft tissue other than fat is approximately 20 millimeters. Thus, a plane wave of microwave energy of this frequency may be useful for the treatment of keratinized tissue that is thick, e.g. a hoof. Accordingly, to restrict penetration, a higher frequency could be used, as described above.

In some embodiments, the applicator comprises more than one metallic conductor separated by a distance much less than half a wavelength. As used herein, the term "much less than half" refers to less than or equal to about 0.25 times a wavelength. By way of non-limiting example, microwave energy can be coupled into keratinized tissue by bringing metallic conductors into proximity or contact with it. The depth of penetration of microwave energy into tissue can be controlled by the spacing of the metallic conductors in contact with the tissue. In this way, the depth of penetration can be set to a value suited to the anatomical site of treatment. Swicord and Davis (*IEEE Trans. On Microwave Theory And Techniques* 29(11):1202-1208, 1981) teach that closely-spaced metallic conductors in proximity to tissue produce a fringing pattern of microwave fields that penetrate a lesser distance, the total distance being determined by the spacing of metallic conductors. As used herein, "closely-spaced" means much less than a half-wavelength, e.g., much less than a quarter-wavelength. The teachings of Swicord and Davis have been applied successfully, for example, to heat the cornea of the eye without over-heating the endothelial cells on the posterior surface of the cornea. Trembly and Keates (Trembly B S and Keates R H, *IEEE Transactions on Biomedical Engineering* 38(1):85-91, 1991) teach that in this case the penetration of microwave energy of 915 MHz was restricted to a few tenths of a millimeter to suit the anatomy. The same technique would be appropriate for heating a thin layer of keratinized tissue, such as a nail, across its narrow dimension from a position in contact or proximity to its surface. As used herein, the term "metallic conductor" refers to material or an object that permits an electric current to flow easily. It is to be appreciated that in certain embodiments, the metallic conductors can be made of copper, brass, silver, gold, aluminum, stainless steel or any other material that one of skill in the art, having the benefit of this disclosure, would use.

Figure 6:
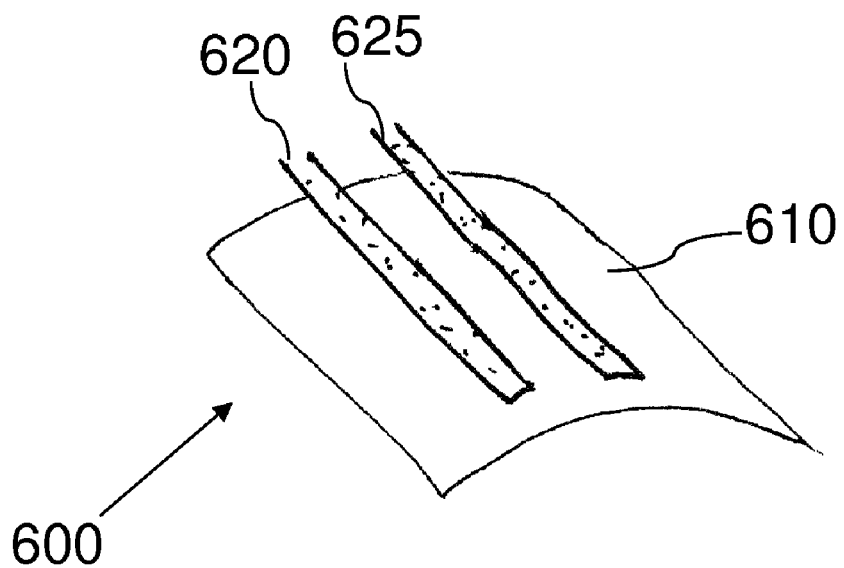
FIG. 6 is a schematic of an applicator 600 comprising a flexible substrate 610 to allow conformance to keratinized tissue, such as nail tissue, that includes two metallic conductors 620 and 625 spaced apart by much less than a wavelength, in accordance with certain aspects.
Figure 7:
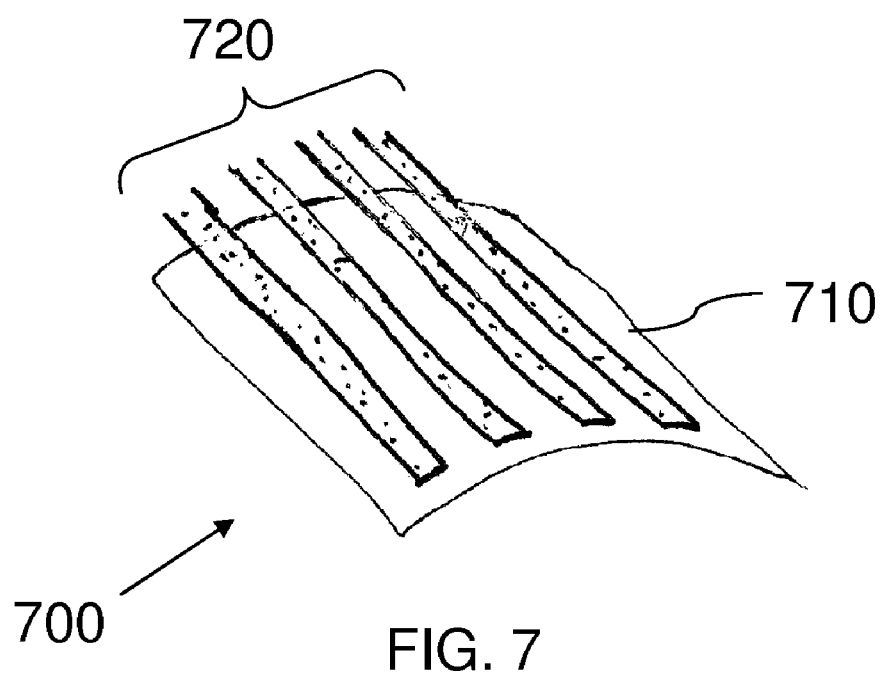
FIG. 7 is a schematic of an applicator 700 comprising a flexible substrate 710 to allow conformance to keratinized tissue, such as nail tissue, that includes a plurality of metallic conductors 720 spaced apart by much less than a wavelength, in accordance with certain aspects.
Figure 8:
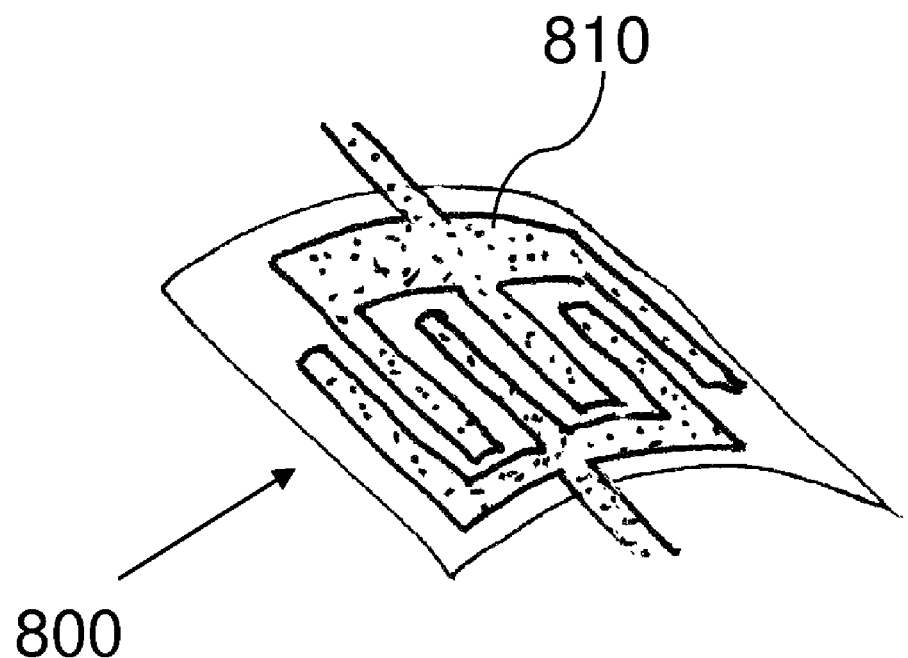
FIG. 8 is a schematic of an applicator 800 comprising an interdigitated geometry 810, in accordance with certain aspects.
Figure 16:
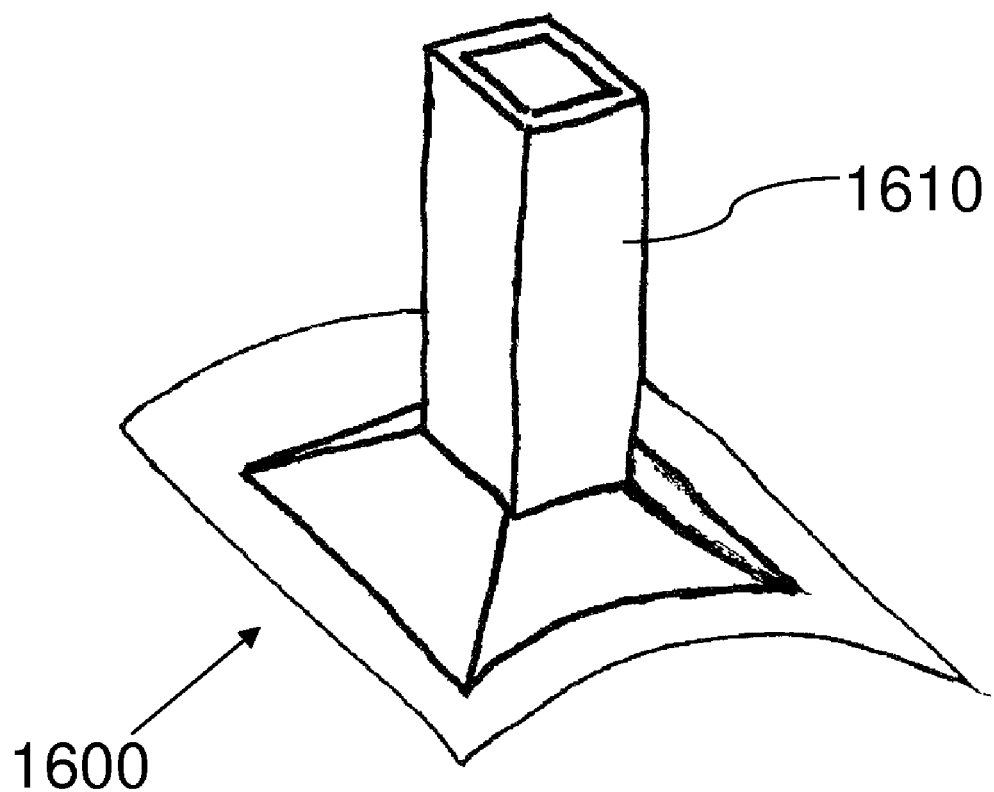
FIG. 16 is a schematic of an applicator 1600 wherein the applicator has at least one conductor having the shape of a horn 1610 and having a diameter anywhere in a range of about 2 mm to 40 mm, in accordance with certain aspects; and It will be recognized by the person of ordinary skill in the art, given the benefit of this disclosure, that the figures are not necessarily to scale and that certain features of the figures may have been enlarged, distorted or emphasized to facilitate a better understanding of the illustrative aspects and examples described in more detail below.

In certain embodiments, the applicator has from about 2 to about 40 metallic conductors (see, for example, FIGS. 6 and 7). Referring to FIG. 6, an applicator 600 comprises a flexible substrate 610 and two metallic conductors 620 and 625. Referring to FIG. 7, an applicator 700 comprises a flexible substrate 710 and a plurality of metallic conductors 720. In some embodiments, the metallic conductors of the applicator have a length from about 5 to about 40 mm and a width of about 0.25 mm to about 2 mm. In some embodiments, the applicator has an interdigitated geometry (see FIG. 8 showing an applicator 800 that includes an interdigitated geometry 810) having a spacing between metallic conductors of about 0.25 mm to about 2 mm. In some embodiments, the applicator has 2 conductors having a spacing of about 0.25 mm to 2 mm which meander in the plane defined by the surface of the tissue to be heated. In some embodiments, the applicator has a single conductor having the shape of a horn (see the horn 1610 of the applicator 1600 in FIG. 16) of diameter about 2 mm to 40 mm. By way of example, suitable metallic conductors can be obtained from, e.g., Small Parts, Inc. (Miami Lakes, Fla.). The term "about" as used herein refers to a variance of 20% from the identified value, for the lower and higher values. For example, if a numerical range is given as from about 10 to about 20, it will be understood that the lower value may range from 8 to 12 and the higher value may range from 16 to 24. By way of non-limiting example, a practical example of closely-spaced metallic conductors would be an interdigitated geometry designed to cover the surface of a nail.

Figure 9:
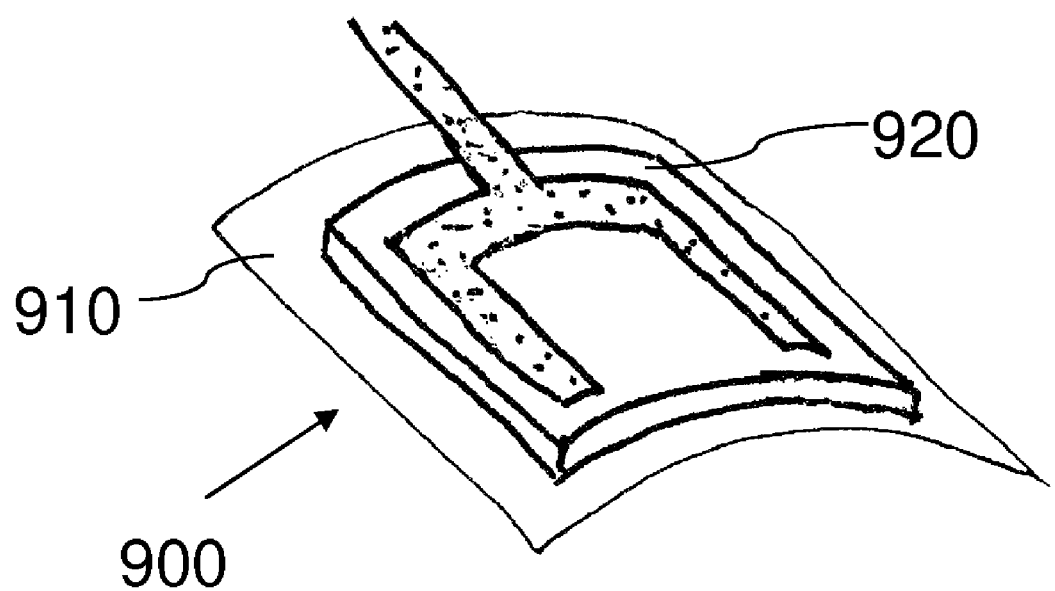
FIG. 9 is a schematic of an applicator 900 comprising a substrate 910 that includes an adhesive 920 to permit adherence to a surface, in accordance with certain aspects.

In certain embodiments, the applicator further comprises an adhesive to permit adherence to a surface (see, for example, the adhesive 920 on the substrate 910 shown in the applicator 900 of FIG. 9). Suitable adhesives will be readily selected by the person of ordinary skill in the art, given the benefit of this disclosure. In some embodiments, the metallic conductors and substrate are sufficiently thin to permit trimming to an arbitrary shape in a plane with an instrument such as shears. In some embodiments, the metallic conductors and substrate are sufficiently flexible to permit conformance to a curved anatomical site (see FIGS. 6 and 7). In certain examples, the applicator may have double-sided adhesive tape to provide adherence to a surface. The double-sided adhesive tape can be removed easily from the applicator and replaced with new double-sided adhesive tape to facilitate use of the same applicator with different patients without having to sterilize the applicator.

Figure 15:
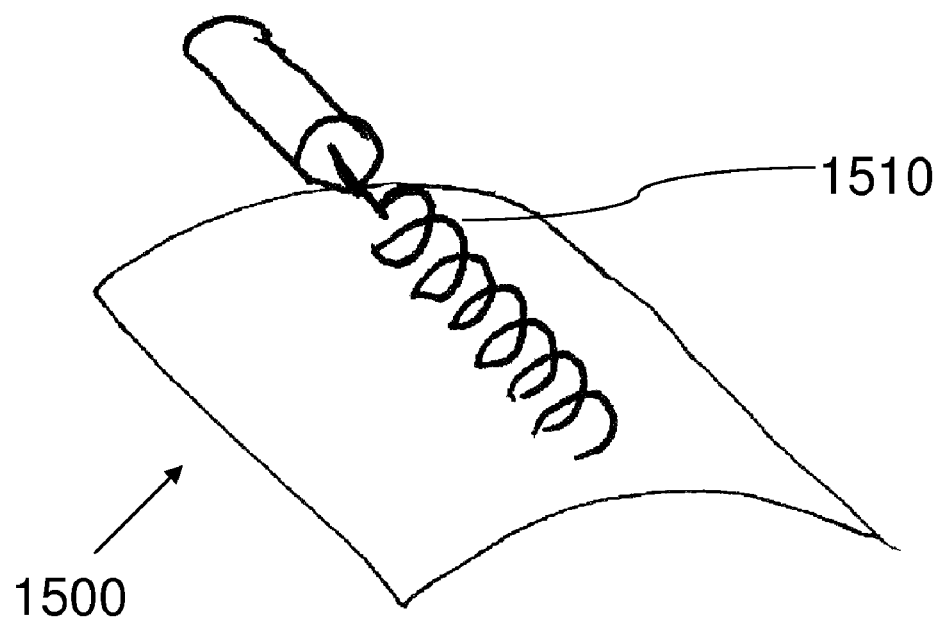
FIG. 15 is a schematic of an applicator 1500 wherein one or more of the conductors is configured with a helical coil geometry 1510, in accordance with certain aspects.

In some embodiments, one or more helical coil antennas are used to heat the tissue (see, for example, the applicator 1500 including a helical coil 1510 as shown in FIG. 15). Ryan, T P "Comparison of six microwave antenna for hyperthermia treatment of cancer: SAR results for single antenna and array," International Journal of Radiation Oncology, Biology, and Physics 21:403-413, 1991) teaches that the helical coil applicator has a rapid decrease in energy deposition with distance from the antenna, as compared to a conventional dipole. U.S. Pat. No. 4,967,765 issued Nov. 6, 1990 to Turner, et al. teaches the use of a helical coil applicator to heat the prostate from a position within the urethra. U.S. Pat. No. 4,825,880 issued May 2, 1989 to Stauffer et al. teaches the use of a helical coil applicator for heating cancerous tissue from within the body. None of the citations listed immediately above teaches the use of a helical coil antenna to heat keratinized tissue infected with a pathogen.

Figure 10:
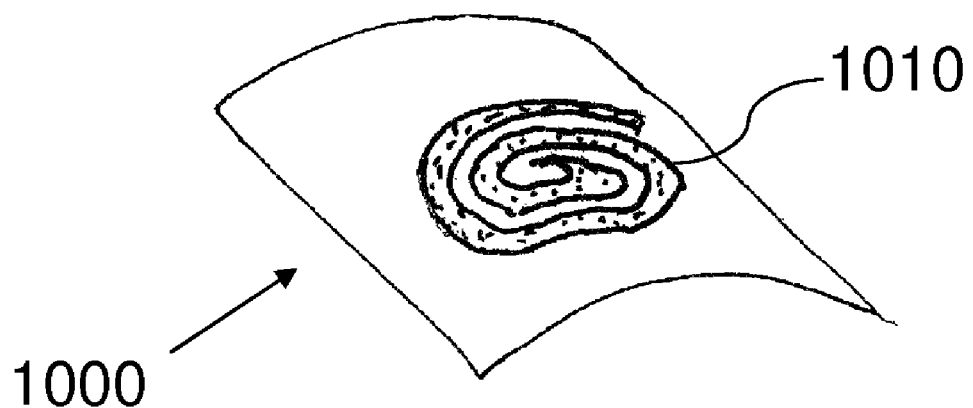
FIG. 10 is a schematic of an applicator 1000 wherein one or more of the conductors have a spiral geometry 1010, in accordance with certain aspects.
Figure 11:
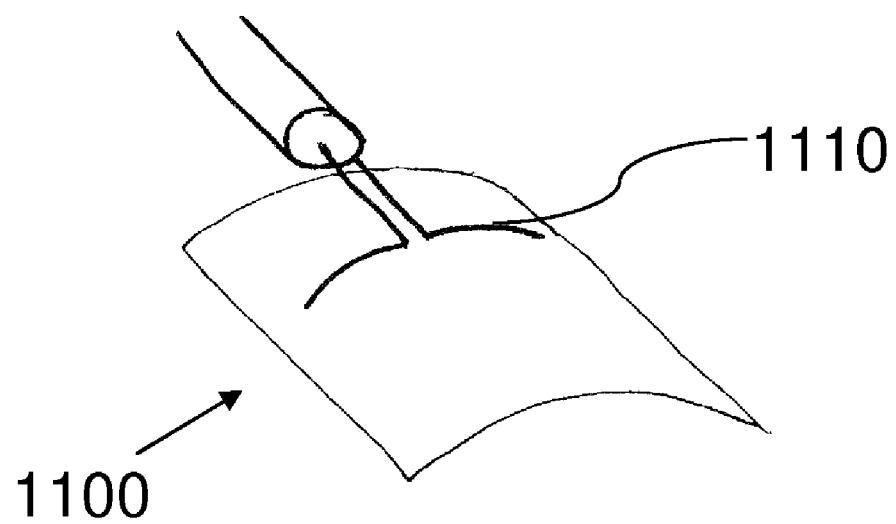
FIG. 11 is a schematic of an applicator 1100 wherein two of the conductors comprise a dipole geometry 1110, in accordance with certain aspect.
Figure 12:
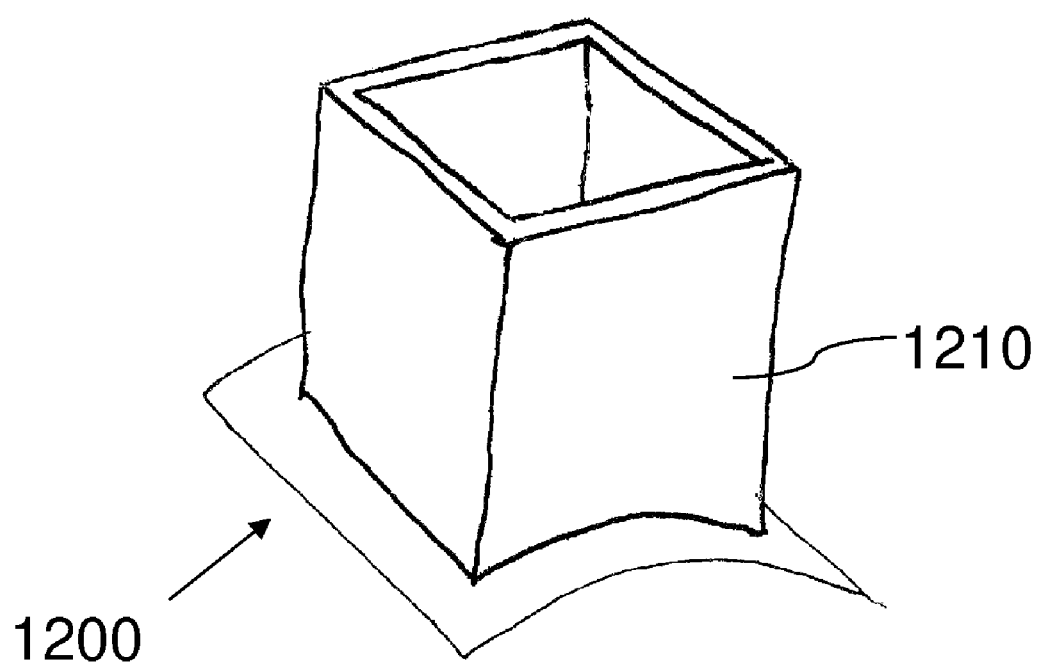
FIG. 12 is a schematic of an applicator 1200 wherein each conductor is configured with a waveguide geometry 1210, in accordance with certain aspects.
Figure 13:
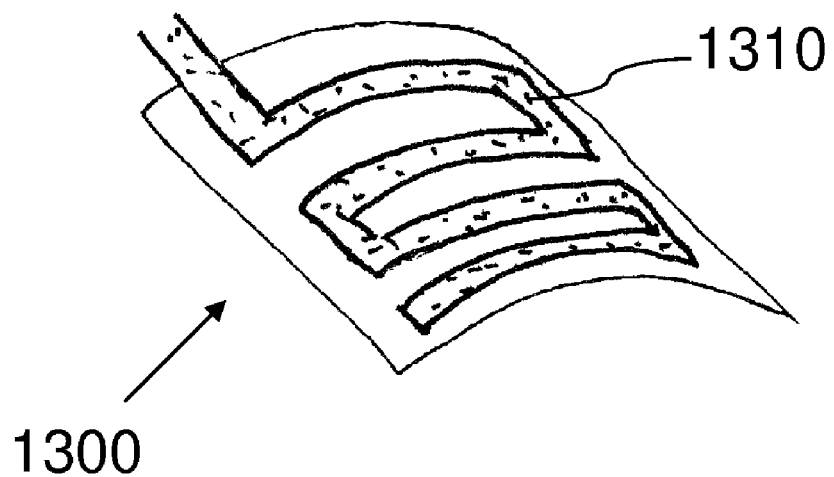
FIG. 13 is a schematic of an applicator 1300 wherein one or more of the conductors is configured with a meandering geometry 1310, in accordance with certain aspects.
Figure 14:
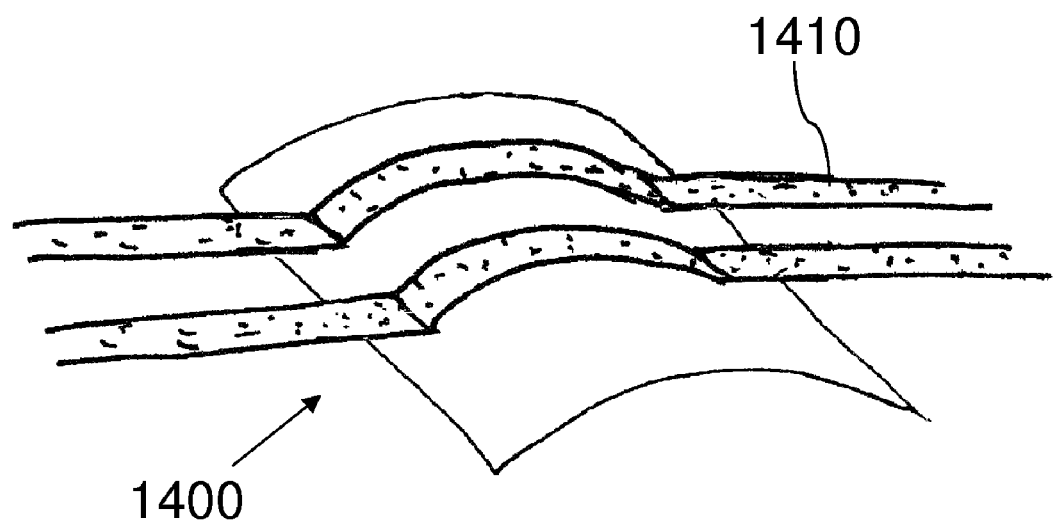
FIG. 14 is a schematic of an applicator 1400 wherein a pair of conductors is configured with a transmission line geometry 1410, in accordance with certain aspects.

In some embodiments, one or more conductors have a spiral geometry 1010 as shown, for example, in the applicator 1000 of FIG. 10. In some embodiments, one or more conductors have a meandering geometry 1310 as shown, for example, in the applicator 1300 in FIG. 13. In some embodiments, pairs of conductors have dipole geometry 1110 as shown, for example, in the applicator 1100 in FIG. 11). In some embodiments, each conductor of the applicator has geometry chosen from the group comprising waveguides (see, for example, the waveguide geometry 1210 of the applicator 1200 of FIG. 12) and horns (see, for example, the horn 1610 shown in the applicator 1600 of FIG. 16). In some embodiments, the radiation device comprises a horn antenna, a waveguide antenna, or any other antenna or radiating device that one of skill in the art, having the benefit of this disclosure, would use. In certain examples, a pair of conductors may be configured with a transmission line geometry such as, for example, an applicator 1400 including a transmission line geometry 1410 as shown in FIG. 14.

In an alternative embodiment, the metallic conductors or radiating device may form a partially or completely closed chamber that surrounds the tissue, e.g., a hoof, such as the configuration of a microwave oven. For example, electromagnetic energy can be provided to a central cavity through a cable or waveguide inlet. A hoof or appendage to be treated can be inserted into the applicator, and electromagnetic energy is supplied for treatment.

The examples below are intended to further illustrate certain preferred embodiments and are not intended to limit the scope of the invention.

EXAMPLES

Example 1

Preliminary Testing

Two examples were performed: 1) *Trichophyton* species was isolated from nail tissue and was identified at Emerson Hospital Mycology Lab by conventional methods. The fungus was plated on BBL Sab Dex Emmons dish (CM41, Oxoid Inc., Ogdensburg, N.Y.) and exposed to 2450 MHz microwave energy at 1100 watts (Panasonic Household Microwave Oven NN-S668BA) for varying lengths of time. No growth was found at exposures greater than 10 seconds. 2) Toe nail clippings that had previously been shown by periodic acid schiff stain (PAS) to contain fungus were exposed to 2450 MHz at 1100 watts of microwave energy for varying lengths of time. Fungal isolation was carried out at room temperature on BBL Sab Dex Emmons dish (CM41, Oxoid Inc., Ogdensburg, N.Y.) with and without chloramphenicol (0.05 g/L) and cycloheximide (5 g/L). After 21 days of culturing, no growth was seen at exposures greater than 1 minute.

Example 2

Determination of a Kill-Dose Microwave Energy Level

The following methods were used. The dermatophyte was obtained from the clipped toe nail sample of a human patient with clinically diagnosed onychomycosis. Fungus was confirmed in the sample by microscopy with the PAS stain, and cultured onto Sabouraud's dextrose agar with/without chloramphenicol and cycloheximide for 4 weeks, identifying the fungus as a *Trichophyton* spp. Using sterile techniques the nail samples were prepared using a #11 scalpel to scrape off the white keratin debris from the infected nail. Samples of nail debris of length 4 mm were then loaded into sterilized 2 mm diameter polyurethane tubing and closed with phenolic plugs. A total of 51 samples were made.

The vial to be treated was placed within a plexiglass vial carrier designed to position the nail sample at one of the locations of the maximum electric field inside of a slotted line (Hewlett Packard Model 805C). This apparatus consisted of an 11 mm diameter cylindrical inner conductor fixed centrally between two vertical plates that together form the outer conductor. The electric field was greatest at the point of closest approach between the inner and outer conductors, a gap of 4.5 mm. The slotted line was terminated with an open circuit, producing a standing wave pattern along the long axis of the slotted line. The axial location of a maximum of electric field was measured with the electric field probe integral to the slotted line. A maximum was found at a distance equal to a half-wavelength (164 mm) from the point of the open circuit termination, as predicted by transmission line theory.

The slotted line was driven by a 915 MHz generator (American Microwave Technologies Model 1120) through 6 feet of RG-214/U cables. The generator in turn was controlled by a purpose-built proportional-integral controller that compared the set-point of power to the actual value measured by a dual directional coupler (Narda Model 3020A) and power meter (Hewlett Packard Model 435B). The generator was protected from reflected power by a circulator (Pamtech Model 1146) terminated with a load (Narda Model 369 BNF, 175 watt rating). Samples contained in vials 1 to 25 were exposed to 5 minutes of heating with a forward power of 68 watts. Samples in vials 26 to 51 were used as controls.

The samples were then separately inoculated onto Dermatophyte Test Medium (Acu-DTM, Acuderm, Inc., Ft. Lauderdale, Fla.). They were incubated at room temperature. The test medium was examined for color change and colony growth daily for two weeks. A positive result was declared when the test medium changed from yellow to red with or without concurrent colony growth. A negative result was declared when there was no color change. Of the treated samples, after 14 days, $1/25$ showed the presence of viable dermatophytes. Of the control samples, after 14 days, $13/25$ showed the presence of viable dermatophytes. There was no colony growth noted without color change on the DTM medium. There was no color change without colony growth. A chi-squared analysis of the data was performed. Using an alpha level of 0.05 there was a significant difference in the growth proportions across the 2 treatment conditions. In addition, the effect size (Cramer's V) is high. At 30 days the samples were reexamined. There was no new growth among the treated samples, and 2 additional samples among the controls showed growth.

The results of this experiment are consistent with the use of 68 Watts, for 5 minutes, of microwave irradiation in the slotted line apparatus described above, as a kill-dose for a dermatophyte, *Trichophyton* spp., in a keratin substrate. The main part of the experiment was stopped after 14 days because color interpretation of the Dermatophyte Test Medium is questionable after this due to the possibility of false positives and fewer than 2% of cultures require 2 weeks to show a change in color. The 30 day evaluation was used to answer the question of whether the irradiation delayed growth rather than provided a kill-dose. The low growth rate was consistent with the previously described 30% positive microscopy and culture results due to sampling errors from infected nails. This was higher in our experiment probably because of the particularly small sample size required by the 2 mm diameter polyurethane tubing.

Example 3

Determination of a Kill-Dose Microwave Energy Level with a Prototype Applicator

The methods of Example 2 were used, except that the microwave applicator consisted of a coaxial cable with a portion of the outer conductor removed. Vials of fungal-infected tissue were placed in proximity to the inner conductor of the coaxial cable. Five vials were treated at each of the following power levels: 25 watts, 40 watts, 55 watts; in every case, the duration of heating was 5 minutes. Eleven untreated vials served as controls. Fungal growth was observed in 7 of 11 control vials after 14 days. No fungal growth was observed in any treated vial, regardless of power level. Using an alpha level of 0.05 there was a significant difference in the growth proportions across the 4 treatment conditions.

Equivalents

While the foregoing invention has been described in some detail for purposes of clarity and understanding, it will be appreciated by one skilled in the art from a reading of this disclosure that various changes, substitutions, and modifications in form and detail can be made without departing from the true scope of the invention and appended claims.

The issued patents, patent applications, and references that are cited herein are hereby incorporated by reference to the same extent as if each was specifically and individually indicated to be incorporated by reference. In the event of inconsistencies between any teaching of any reference cited herein and the present specification, the latter shall prevail for purposes of the invention.

What is claimed is:

1. A method for treating nail tissue infected with a pathogen comprising exposing the nail tissue to an effective amount of electromagnetic energy having a wavelength greater than about 0.1 mm, sufficient to kill the pathogen infecting the nail tissue.

2. The method of claim 1, wherein the pathogen is a fungus.

3. The method of claim 1, wherein the pathogen is a bacterium.

4. The method of claim 1, wherein the pathogen is a parasite.

5. The method of claim 1, wherein the effective amount of electromagnetic energy is within a range from about 0.1 milliwatt/$cm^2$ to 1000 milliwatt/$cm^2$.

6. The method of claim 1, wherein the electromagnetic energy has a wave frequency from about 15 MHz to about 10 GHz.

7. The method of claim 1, wherein the electromagnetic energy has a wave frequency from about 15 MHz to about 30 GHz 8. The method of claim 1, wherein the electromagnetic energy has a wavelength greater than about 10 mm.

9. The method of claim 1 wherein the electromagnetic energy has a wave frequency of about 2.45 GHz.

10. The method of claim 1, wherein the nail tissue is human nail tissue.

11. The method of claim 1, wherein the method further includes cooling of underlying tissue by way of reactive hyperemia.

12. The method of claim 1, wherein the method further includes measuring tissue temperature during the application of the electromagnetic energy.

13. The method of claim 12, wherein the method further includes measuring tissue temperature by way of microwave radiometry.

14. The method of claim 1, wherein exposing the nail tissue to the electromagnetic energy is operative to stimulate the immune system of the patient.

15. The method of claim 1, wherein exposing the nail tissue to the electromagnetic energy is preceded by a heating process that stimulates blood perfusion in the vicinity of the nail tissue.

16. The method of claim 1, wherein the method further includes administering an effective amount of a therapeutic.

17. The method of claim 1, wherein the method further includes exposing the nail tissue to the electromagnetic energy using an applicator.

18. The method of claim 17, wherein the method further includes placing an electrically-conductive material between the applicator and nail tissue to prevent absorption of the electromagnetic energy in the nail tissue.

19. The method of claim 17, wherein the method further includes placing an energy-absorbing material between the applicator and the nail tissue to reduce absorption of the electromagnetic energy.

20. The method of claim 1, wherein the exposing the nail tissue includes applying the electromagnetic energy to the nail tissue before clinical symptoms of pathogen infection have appeared.

21. An applicator for the delivery of electromagnetic energy to keratinized tissue infected with a pathogen comprising a flexible substrate to allow conformance to a curved surface of the keratinized tissue, the applicator further comprising two or more metallic conductors configured to provide electromagnetic energy having a wavelength greater than about 0.1 mm, wherein the conductors have an interdigitated geometry.

22. The applicator of claim 21, wherein the substrate has an adhesive to permit adherence to a surface.

23. An applicator for the delivery of electromagnetic energy to keratinized tissue infected with a pathogen comprising a flexible substrate to allow conformance to a curved surface of the keratinized tissue, the applicator further comprising two or more metallic conductors configured to provide electromagnetic energy having a wavelength greater than about 0.1 mm, wherein one or more of the conductors have a spiral geometry.

24. An applicator for the delivery of electromagnetic energy to keratinized tissue infected with a pathogen comprising a flexible substrate to allow conformance to a curved surface of the keratinized tissue, the applicator further comprising two or more metallic conductors configured to provide electromagnetic energy having a wavelength greater than about 0.1 mm, wherein one or more of the conductors is configured with a meandering geometry.

25. An applicator for the delivery of electromagnetic energy to keratinized tissue infected with a pathogen comprising a flexible substrate to allow conformance to a curved surface of the keratinized tissue, the applicator further comprising two or more metallic conductors configured to provide electromagnetic energy having a wavelength greater than about 0.1 mm, wherein one or more of the conductors is configured with a helical coil geometry.

26. The applicator of claim 21, wherein the interdigitated geometry has a spacing between metallic conductors of anywhere in a range from about 0.25 mm to about 2 mm.

27. An applicator for the delivery of electromagnetic energy to keratinized tissue infected with a pathogen comprising a flexible substrate to allow conformance to a curved surface of the keratinized tissue, the applicator further comprising two or more metallic conductors configured to provide electromagnetic energy having a wavelength greater than about 0.1 mm, wherein the applicator has at least one conductor having the shape of a horn and having a diameter anywhere in a range of about 2 mm to 40 mm.

* * * * *